United States Patent [19]

Dhabhar et al.

[11] 4,289,754
[45] Sep. 15, 1981

[54] ZINC DERIVATIVES AND THEIR USE IN MOUTHWASH COMPOSITIONS

[75] Inventors: Dadi J. Dhabhar, Norwalk, Conn.; Nutan B. Shah, New Rochelle, N.Y.

[73] Assignee: Richardson-Vicks Inc., Wilton, Conn.

[21] Appl. No.: 203,520

[22] Filed: Nov. 3, 1980

[51] Int. Cl.$^3$ .................. A61K 7/16; A61K 7/18; A61K 7/24

[52] U.S. Cl. ............................ 424/52; 424/49; 424/55

[58] Field of Search ....................... 424/49-58

[56] References Cited

U.S. PATENT DOCUMENTS

| | | | |
|---|---|---|---|
| 3,772,431 | 11/1973 | Mlkvy et al. | 424/49 |
| 3,888,976 | 6/1975 | Mlkvy et al. | 424/49 |
| 4,022,880 | 5/1977 | Vinson et al. | 424/49 |
| 4,082,841 | 4/1978 | Pader | 424/52 |
| 4,100,269 | 7/1978 | Pader | 424/49 |
| 4,138,477 | 2/1979 | Gaffar | 424/52 |
| 4,144,323 | 3/1979 | Lamberti | 424/49 |
| 4,152,418 | 5/1979 | Pader | 424/50 |
| 4,154,815 | 5/1979 | Pader | 424/50 |
| 4,229,430 | 10/1980 | Fahim et al. | 424/49 |

*Primary Examiner*—Shep K. Rose
*Attorney, Agent, or Firm*—George W. Rauchfuss, Jr.

[57] ABSTRACT

A novel zinc compound, an alkali metal or ammonium zinc citrate, is prepared for use in mouthwash compositions to provide mouthwashes with less astringency without loss of anti-odor properties, improved water solubility of the zinc compound and improved chemical compatibility when ionic fluoride salts are employed in compositions along with the zinc compound.

8 Claims, No Drawings

ZINC DERIVATIVES AND THEIR USE IN MOUTHWASH COMPOSITIONS

FIELD OF THE INVENTION

This invention relates to a novel zinc compound and the use thereof in mouthwash compositions.

BACKGROUND OF THE INVENTION

The beneficial effect of zinc compounds in dental compositions, especially in toothpastes and mouthwashes, has been generally recognized for some time. In U.S. Pat. No. 4,100,269, issued July 11, 1978 to Morton Pader, there is disclosed the use of insoluble zinc compounds in dentifrices for improving the control of calculus. Insoluble zinc compounds employed in the patent are those having a solubility of less than about one gram of zinc per 100 cc of water at 20° C. and preferably a solubility of not more than about 0.5 gram zinc compound per 100 cc water at 20° C. Among the typical insoluble zinc compounds employed in the patent is zinc citrate. Zinc acetate and hydroxide have been recognized as having anti-plaque properties in dentifrices as disclosed in Hanke, M. T., J. Amer. Dental Assoc., 27(9), 1379-93 (1940). The pyrophosphate, tetrametaphosphate, metaphosphate and orthophosphate salts of zinc have been known to be effective in tartar removal as disclosed in W. German Pat. No. 1,251,468, assigned to Chemische Fabrik Budenheim and published Oct. 5, 1967. Also it has been known to formulate tooth powders containing zinc citrate and calcium gluconate such as disclosed in U.S. Pat. No. 1,861,189 issued May 31, 1932 to Charles Pfizer.

In addition, zinc chloride has been used in mouthwash compositions and recognized as possessing anti-mouth odor properties in said compositions.

However, despite the heretofore known use of zinc compounds in dental compositions their use has not been without certain undesirable drawbacks and side-effects. For example, when such zinc compounds have been employed it has not been possible to satisfactorily include ionic fluoride in the compositions due to the chemical incompatibility therebetween. Moreover, while zinc chloride possesses the desired anti-odor activity, its high level of astringency is undesirable. Yet other zinc compounds, such as for example, zinc citrate are so slightly soluble in aqueous solutions that while the level of astringency is kept acceptably low, there is an undesirable loss in anti-mouth odor activity of the zinc compound.

It is therefore highly desirable to provide a zinc derivative that is less astringent than zinc chloride so as to provide enhanced acceptance by users of dental compositions containing same yet without sacrificing anti-odor activity. It is also desirable to provide a zinc derivative having higher aqueous solubility than zinc citrate yet not as astringent as zinc chloride. Additionally it is desirable to provide a zinc derivative of said properties that does not present substantially any chemical incompatibility problem in dental compositions employing an ionic fluoride salt.

BRIEF DESCRIPTION OF THE INVENTION

In accordance with the invention a novel zinc derivative, an alkali metal or ammonium zinc citrate, and preferably, sodium zinc citrate, possessing such desired properties is provided and permits the formulation of mouthwash compositions containing an ionic fluoride compound and possessing improved properties.

DETAILED DESCRIPTION OF THE INVENTION

An alkali metal or ammonium zinc citrate, $C_6H_5O_7MZn$, wherein M is ammonium or an alkali metal, preferably sodium or potassium, is prepared by the reaction of equimolar amounts of ammonium hydroxide or an alkali metal hydroxide, such as sodium hydroxide, with zinc oxide and citric acid. The reaction can be carried out, for example, at room temperature in water as per the following Example.

EXAMPLE

In a reaction vessel 21.04 g citric acid, hydrous, is dissolved in 100 g water. To this solution 8.14 g zinc oxide is added in small quantities and the reaction mixture stirred. After the reaction of the zinc oxide with the citric acid 4.0 g sodium hydroxide is added and the reaction mixture stirred until all the sodium hydroxide is reacted. At the end of the reaction, a clear solution is obtained. The solution is treated with absolute ethyl alcohol to precipitate out the sodium zinc citrate salt. The salt crystals are filtered off and dried overnight in a 45° C. oven. Elemental Analysis. Calculated: Zn, 20.8; C, 22.90; H, 2.88; Na, 7.30. Found: Zn, 22.1; C, 22.84; H, 3.13; Na, 5.70. The pH of a 2.5% suspension of the salt is 6.32 and the solubility of the salt in water at 25° C. is 1.17 g/100 ml.

In a similar manner other alkali metal zinc citrate salts can be prepared by the use of other alkali metal hydroxides or ammonium hydroxide in place of sodium hydroxide in the Example, such as for example, potassium zinc citrate is prepared when potassium hydroxide is employed.

The ammonium or alkali metal zinc citrate compounds of this invention are especially useful in mouthwash compositions. The new compounds, especially sodium zinc citrate, is considerably less astringent than zinc chloride which is now used in mouthwash compositions and, therefore, is of greatly enhanced acceptability yet without sacrificing its anti-odor property. Furthermore, the compounds of this invention possess high aqueous solubility and permits one to formulate concentrated mouthwash formulations. Additionally, the compounds of this invention can be added to dentifrice compositions, such as mouthwashes, containing an ionic fluoride salt and without any significant chemical instability. The novel compounds can be added to mouthwash compositions or be formed in situ in mouthwash compositions from zinc oxide, citric acid and the hydroxide.

In mouthwash compositions the zinc compounds of this invention are employed in amounts of from about 0.1 to about 15.0%, preferably about 0.2 to about 5%, and most preferably about 0.5 to about 2.0%, by weight based on the total weight of the composition so as to provide from about 7 to about 28 mg/kg body weight of the user thereof. The mouthwash compositions of this invention have present ionic fluoride compounds possessing anticaries activity, such as for example, sodium fluoride, potassium fluoride, stannous fluoride and sodium monofluorophosphate. The fluoride compounds are employed as the mouthwash compositions of this invention in amounts whithin the range of from about 0.01 to about 1.0% by weight. The mouthwash compositions of the present invention comprise the aforesaid ammonium or alkali metal zinc citrate salt, an ionic fluoride compound and a carrier suitable for use in the oral cavity. The carrier can be water or an organic solvent such as alcohol.

Mouthwashes generally comprise a water/ethyl alcohol solution and optionally other ingredients such as flavor, sweeteners, and humectants. The alcohol provides an antibacterial effect. Optionally, mouthwashes also contain sudsing agents. Humectants such as glycerine and sorbitol give a moist feel in the mouth and are desirably also present. Antibacterial agents are sometimes incorporated into mouthwashes or dentifrices at levels from about 0.01% to about 2.0% by weight.

Generally, mouthwashes suitable for use as carriers herein contain: 5% to 40% ethyl alcohol; 0% to 20%, preferably 5% to 20%, glycerine or other humectant; 0% to 12%, preferably 0.1% to 12%, sudsing agent, 0% to 0.5%, preferably 0.05% to 0.5%, sweetening agent such as saccharin; and 0% to 0.3%, preferably 0.05% to 0.3%, flavoring agent; and the balance, water with colorants or dyes if desired.

Mouthwashes usually contain surface-active agents also called sudsing agents. Suitable surface-active agents are those which are reasonably stable and form suds throughout a wide pH range, that is, nonsoap nonionic, cationic, and amphoteric organic synthetic detergents.

The nonionic synthetic detergents which can be used with the mouthwash compositions of the present invention may be broadly defined as compounds produced by the condensation of a hydrophilic alkylene oxide group with an organic hydrophobic compound which may be aliphatic or alkyl-aromatic in nature. The length of the hydrophyllic or polyoxyalkylene radical which is condensed with any particular hydrophobic group can be readily adjusted to yield a water-soluble compound having the desired degree of balance between hydrophilic and hydrophobic elements.

For example, a well-known class of nonionic synthetic detergents is made available on the market under the trade name of "Pluronic." These compounds are formed by condensing ethylene oxide with a hydrophobic base formed by the condensation of propylene oxide with propylene glycol.

Other suitable nonionic synthetic detergents include: the polyethylene oxide condensates of alkyl phenols, those derived from the condensation of ethylene oxide with the product resulting from the reaction of propylene oxide and ethylene diamine, the condensation product of aliphatic alcohols having from 8 to 18 carbon atoms, in either straight chain or branched chain configuration, with ethylene oxide, and the polyoxyethylene derivatives of fatty acid partial esters of sorbitol anhydride and available in the market under the trade name "Tween."

Cationic synthetic detergents useful in the mouthwash compositions of the present invention can be broadly defined as quaternary ammonium compounds having one long alkyl chain containing from about 8 to about 18 carbon atoms such as lauryl trimethylammonium chloride, cetyl pyridinium chloride, cetyl trimethylammonium bromide, di-isobutylphenoxyethyldimethylbenzylammonium chloride, coconutalkyltrimethylammonium nitrite, cetyl pyridinium fluoride, and the like.

The amphoteric synthetic detergents useful in the present invention can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, for example, carboxylate, sulfonate, sulfate, phosphate, or phosphonate.

Many additional nonionic, cationic and amphoteric synthetic detergents are known to the art and can be used as sudsing agents in the compositions herein. Further examples can be found in *McCutcheon's Detergents and Emulsifiers.*

The sudsing agent can be employed at levels ranging from about 0.5% to about 5.0% by weight of the mouthwash composition.

Mouthwashes normally also contain flavoring agents. Suitable flavoring agents for use in the mouthwashes herein include, for example, wintergreen oil (methyl salicylate), oil of peppermint, oil of sassafras (synthetic), and oil of anise. Flavoring agents are present at a level of from 0.01% to 2.0% by weight.

Mouthwashes normally also contain sweetening agents. Suitable sweetening agents for use in mouthwashes include for example saccharin, dextrose and levulose. The sweetening agents are used at levels of from about 0.05% to about 2% by weight.

The pH of the mouthwash compositions of this invention will be in the range of pH 6.0 to 7.2, preferably 6.5 to 7.2.

The invention is further illustrated by the following formulations.

FORMULATION A

A mouthwash in accordance with the present invention is formulated as follows:

| Component | Amount | |
|---|---|---|
| Ethyl alcohol (95% in water) | 5.28 | % v/v |
| Glycerine | 2.0 | % v/v |
| Zinc oxide | 0.13 | % w/v |
| Citric acid, hydrous | 0.5075 | % w/v |
| Sodium fluoride | 0.05 | % w/v |
| Pluronic F-127 | 1.0 | % w/v |
| Tween 80 | 0.10 | % w/v |
| Flavoring | 0.136 | % w/v |
| Saccharin, insoluble | 0.058 | % w/v |
| Sodium hydroxide pellets | 0.1805 | % w/v |
| Color | 1.0 | % v/v |
| Water | q.s. to 100% | w/v |

The mouthwash is prepared by adding to the distilled water the indicated amounts of citric acid, zinc oxide, sodium hydroxide, sodium fluoride and glycerine. To the alcohol there is added the indicated amounts of Pluronic F-127, Tween 80, saccharin and flavoring. The alcohol and water solutions are then combined, the colorant added and mixed with a sufficient quantity of distilled water to produce the mouthwash.

FORMULATION B

A mouthwash in accordance with the present invention is formulated as follows:

| Component | Parts by Weight |
|---|---|
| Ethyl alcohol (95% in water) | 12.00 |
| Cetyl pyridinium chloride | 0.10 |
| Polyoxyethylene (20) sorbitan monooleate | 0.12 |
| Sodium hydroxide (10% in water) | 0.02 |
| Sodium saccharin | 0.055 |
| Flavoring | 0.16 |

-continued

| Component | Parts by Weight |
|---|---|
| Sodium zinc citrate | 0.20 |
| Sodium fluoride | 0.05 |
| Color | 0.50 |
| Sorbitol (70% in water) | 12.00 |
| Distilled water | balance to 100.00 |

We claim:

1. A mouthwash composition comprising about 0.01 to about 1.0% by weight of an anticaries effective fluoride compound and about 0.1 to about 15.0% by weight of an ammonium or alkali metal zinc citrate in a mouthwash carrier suitable for use in the oral cavity.

2. A mouthwash composition of claim 1 wherein the fluoride compound is selected from the group consisting of sodium fluoride, potassium fluoride, stannous fluoride and sodium monoflurophosphate.

3. A mouthwash composition of claim 2 wherein the fluoride compound is sodium fluoride.

4. A mouthwash composition of claim 2 wherein the citrate compound is present in an amount of from about 0.2 to about 5.0% by weight.

5. A mouthwash composition of claim 3 wherein the citrate compound is present in an amount of from about 0.5 to about 2.0% by weight.

6. A mouthwash composition of claim 5 wherein the alkali metal zinc citrate is sodium zinc citrate.

7. A mouthwash composition of claim 5 which is a mouthwash composition comprising about 5 to 40% by weight ethyl alcohol, about 0 to 20% by weight humectant, about 0 to 12% by weight surface active agent, about 0 to 0.5% by weight sweetening agent, about 0 to 0.3% by weight flavoring agent, and the balance water.

8. A mouthwash composition of claim 7 wherein the alkali metal zinc citrate is sodium zinc citrate.

* * * * *